US00PP08091P

United States Patent [19]

Walters, deceased

[11] Patent Number: Plant 8,091

[45] Date of Patent: Jan. 5, 1993

[54] VARIETY OF GERANIUM NAMED PRINCESS

[75] Inventor: Ernest Walters, deceased, late of Hucknall, Great Britain, by Mary Bodill, administrator

[73] Assignee: Oglevee, Ltd., Connellsville, Pa.

[21] Appl. No.: 700,213

[22] Filed: May 13, 1991

[51] Int. Cl.[5] ..... A01H 5/00
[52] U.S. Cl. ..... Plt./87.12
[58] Field of Search ..... Plt./68, 87.12

[56] References Cited

U.S. PATENT DOCUMENTS

P.P. 6,017 9/1987 Kirmann ..... Plt. 87.12

*Primary Examiner*—Howard J. Locker
*Attorney, Agent, or Firm*—Webb, Burden, Ziesenheim & Webb

[57] ABSTRACT

The new variety is characterized by its wiry, but strong, controlled growth habit which enables it to stand upright without artificial support as well as its multitude of small blooms which are slow to shatter.

1 Drawing Sheet

BACKGROUND OF THE INVENTION

The present invention comprises a new and distinct cultivar of *Pelargonium*×*domesticum* known by the varietal name Princess (Oglevee No. 425; Walters No. 37 W-O)). The new variety was discovered by Mr. Ernest Walters in a selected breeding program in Hucknall, Nottingham, Great Britain. The new variety is a selection from the crossing of *P. citrosum, P. acerifolium* and Carisbrooke. The new variety was first asexually reproduced in the United States by cuttings at Oglevee, Ltd., Connellsville, Pa. in January of 1987. The new variety has been asexually reproduced by cuttings of Oglevee Ltd. in Connellsville, Pa. over a several year period. It has also been trialed at Connellsville and has been found to retain its distinctive characteristics through successive propagations.

The cultivar when grown in a glass greenhouse in Connellsville, Pa. using natural light and 60° F. night and 68° F. day, has a response time of 14 weeks from a rooted cutting, not pinched, to flowering in a 6 in. pot. The response time was determined on plants grown in soilless media employing constant fertilizer 150–200 parts per million of nitrogen and potassium in full light. The rooted cuttings were potted on Nov. 1, 1989 and flowered on Feb. 15, 1990.

DESCRIPTION OF THE DRAWING

The accompanying photographic drawing illustrates the new cultivar, with the colors set forth therein being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on 14-week plants blossomed under natural light in a greenhouse and the color readings were taken indoors under 200–220 foot candles of florescent cool white light. Color references are primarily to the RHS Color Chart of The Royal Horticultural Society of London.

THE PLANT

Classification:
- *Botanical.*—*Pelargonium*×*domesticum.*
- *Commercial.*—Regal Geranium.

Form: Neat, mound-like.
- *Height.*—35 cm from media surface.
- *Growth.*—Wiry, strong but controlled growth habit.

Strength: Stands upright without artificial support; continuous flowering.

Foliage: Stalked leaf attachment.

Leaves:
- *Size.*—6.1 cm to 8.2 cm across.
- *Shape.*—Depressed ovate; Base: Reniform.
- *Margin.*—Serrately lobed.
- *Texture.*—Leathery; very pubescent.
- *Color.*—Top: Yellow/Green Group 144A. Bottom: Yellow/Green Group 146C.
- *Ribs and veins.*—Palmate venation. Color: Yellow/Green Group 146C.

Petioles:
- *Color.*—Yellow/Green Group 146B.
- *Length.*—5.5 cm to 6.3 cm.

Stem:
- *Color.*—Yellow/Green Group 146C.
- *Internodes.*—1.0 cm to 1.5 cm in length.

THE BUD

Shape: Elliptical.

Size: 1.5 cm to 2.0 cm in length; bud just beginning to show color.

INFLORESCENCE

Blooming habit: Continuous blooming; multitude of small blooms.
- *Size.*—6.5 cm to 7.0 cm across.
- *Borne.*—Florets on pedicel; pedicel on peduncle.

Florets:
- *Form.*—Cupped.
- *Color.*—Top: Purple Group 77D with a dark blotch on the upper two petals. Center: Blotch-Greyed/Purple Group 187A. Bottom: Purple Group 76C.
- *Petals.*—Five petals in number; separate; not united; margin entire.

*Size.*—3.5 cm to 4.0 cm across when fully open.

*Texture and appearance.*—Smooth (satin like); appearance from a distance is a light lavender flower with a deep purple blotch atop medium green foliage.

Petaloids: None present.

Pedicel:

*Length.*—1.5 cm to 2.0 cm in length.

*Color.*—Yellow/Green Group 146C.

Peduncle: 6.0 cm to 9.0 cm in length.

*Color.*—Yellow/Green Group 146C.

Disease resistance: Not known.

Lasting quality: Very slow to shatter, continuous blooming.

REPRODUCTIVE ORGANS

Stamens:

*Anthers.*—2.0 mm to 3.0 mm in length; 7 to 8 in number.

*Filaments.*—9 mm to 15 mm in length. Color: White at base to a very light pink at tip.

*Pollen.*—Color: Greyed/Orange Group 171A.

Pistils:

*Number.*—One; 5 to 6 part stigma.

*Length.*—16 mm to 18 mm.

*Stigma.*—5 to 6 parted. Color: Red/Purple Group 60C.

*Style.*—1.0 cm. Color: Red/Purple Group 60C.

Ovaries: 5 mm to 6 mm in length; very pubescent; superior.

*Color.*—White to green.

Fruit: None observed.

GENERAL CHARACTERISTICS

This new *Pelargonium*×*domesticum* variety is superior to the current market variety Parisienne. This variety has a neater upright habit, it does not exhibit the procumbent habit of Parisienne. It is easier to root, produces more cuttings and has the ability to withstand abuse with a stronger, wirier plant structure. The flower color is similar to Parisienne but there are many more florets which are slower to shatter providing a longer flower show for the consumer.

It is claimed:

1. A new and distinct variety of Geranium plant substantially as shown and described.

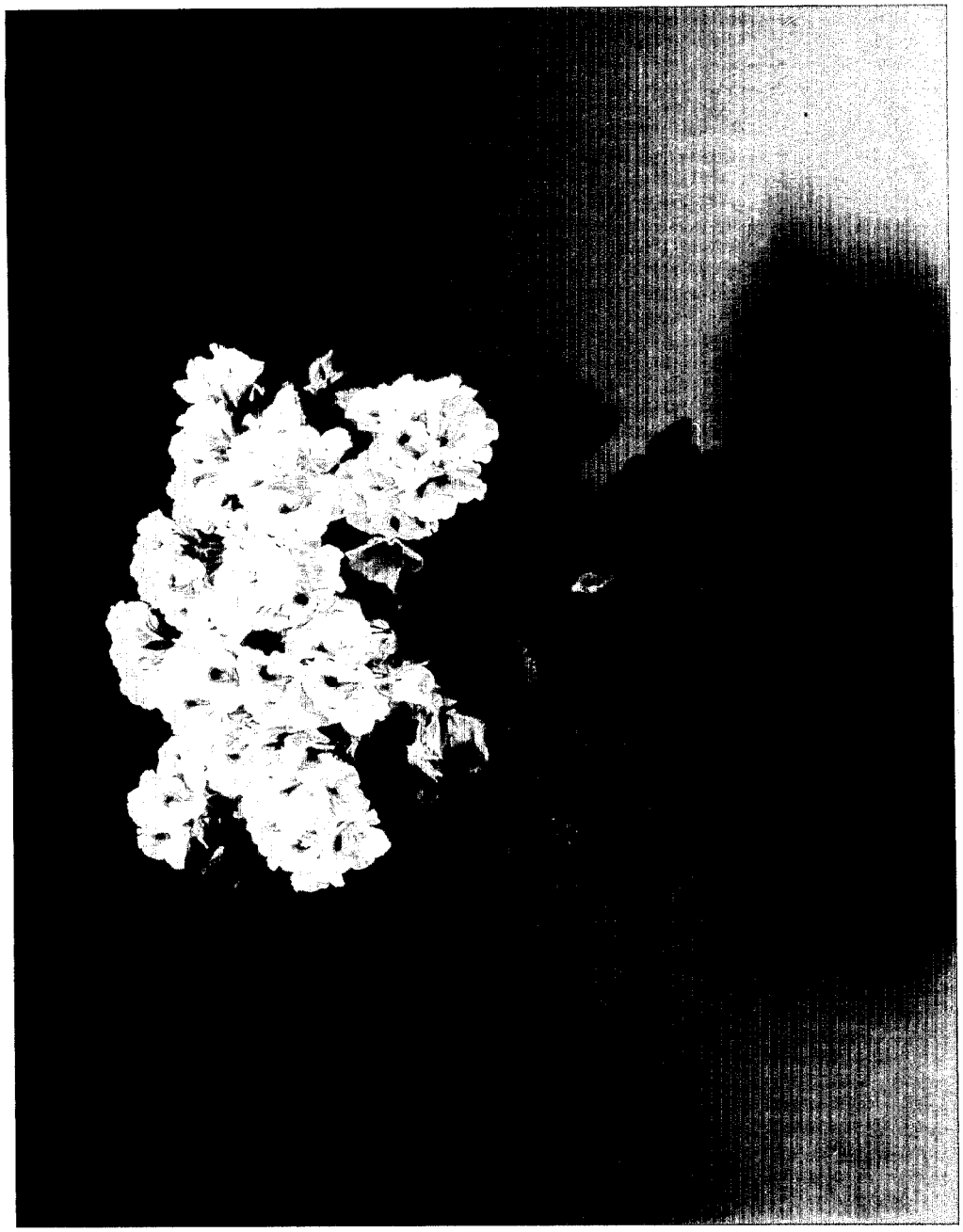

* * * * *